United States Patent [19]

Shaw et al.

[11] Patent Number: 5,672,887
[45] Date of Patent: Sep. 30, 1997

[54] OPTICAL DETECTOR FOR AIR IN FLUID LINE THE SAME

[76] Inventors: Benjamin G. Shaw, #2, 98 Inverness Terr., London, W23LD, England; Tony Joseph Lillios, P.O. Box 1078, Palo Alto, Calif. 94302

[21] Appl. No.: 704,103

[22] Filed: Aug. 28, 1996

Related U.S. Application Data

[63] Continuation of Ser. No. 564,548, Nov. 29, 1995, abandoned.

[51] Int. Cl.$^6$ ............................................. G01N 15/06
[52] U.S. Cl. ........................ 250/573; 250/576; 356/440
[58] Field of Search .......................... 250/573–577, 250/239; 340/619, 627, 632, 634; 128/765–768, DIG. 13, DIG. 22; 356/436, 440, 442

[56] References Cited

U.S. PATENT DOCUMENTS

| | | | |
|---|---|---|---|
| 3,636,360 | 1/1972 | Oishi et al. | |
| 4,366,384 | 12/1982 | Jensen | 250/577 |
| 4,857,050 | 8/1989 | Lentz et al. | 250/577 |
| 4,859,864 | 8/1989 | Smith | 250/577 |
| 4,884,065 | 11/1989 | Crouse et al. | 250/573 |
| 5,206,522 | 4/1993 | Danby et al. | 250/574 |

FOREIGN PATENT DOCUMENTS

| | | |
|---|---|---|
| 0 319 277 A1 | 6/1989 | European Pat. Off. . |
| 2 660 755 A1 | 10/1991 | France . |
| 43 36 520 A | 4/1995 | Germany . |
| WO 86/04409 | 7/1986 | WIPO . |

*Primary Examiner*—Que Le
*Attorney, Agent, or Firm*—Milton Oliver

[57] ABSTRACT

Ambiguity, in readings from an optical bubble detector used with tubing, can be reduced by shaping the tubing into the shape of a prism, so that when different contents of the tubing have differing indices of refraction, there is a clear difference in the exit angle of the light beam leaving the tube. A triangular prism shape is preferred for the compressed tubing. The optical bubble detector features an optics block formed with a V-shaped recess, and a clamp block. The optics block and clamp block cooperatively press or "sandwich" the flexible tubing into the V-shaped recess and deform it into a triangular prismatic cross-section. A generally U-shaped optical interrupter element, containing a photoemitter and a photosensor, fits into the optics block in such a manner that a light beam is directed radially into the triangular tubing section. The clamp block "windows" the transmitted and received light from the optical interrupter, to allow only a thin channel of light to be transmitted; this minimizes optical noise during measurement. When saline is located in the tubing, the light follows a fairly straight path through the optics block and tubing. However, when air is in the tubing, the light is refracted away from the photosensor, resulting in lower intensity readings. By measuring the amount of light received at the photosensor, it can be determined whether air, or saline, is in the tubing.

5 Claims, 8 Drawing Sheets

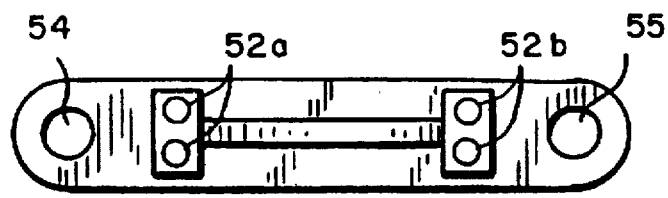
FIG. 15
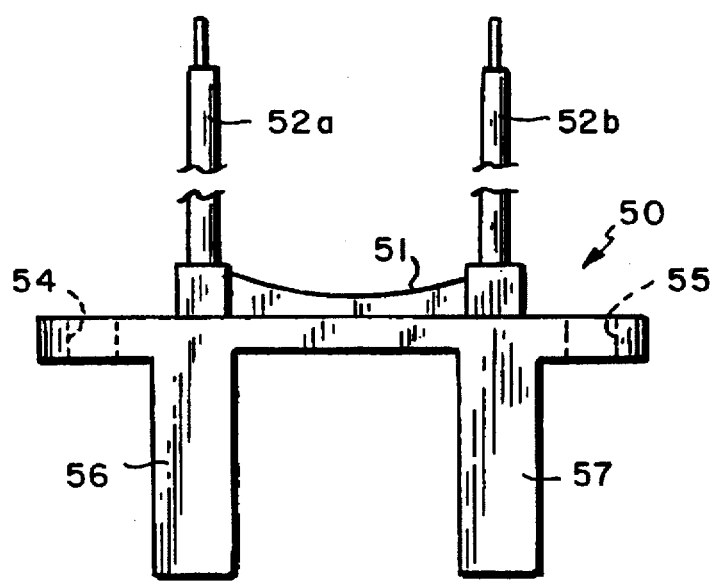 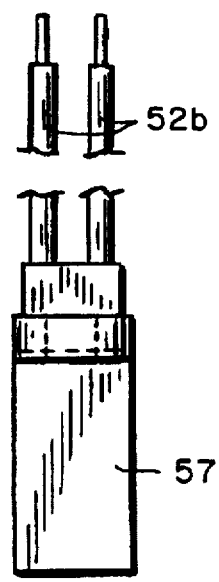
FIG. 13  FIG. 14
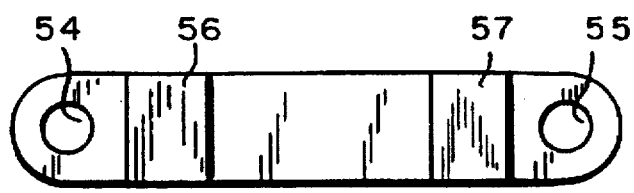
FIG. 16

OPTICAL DETECTOR FOR AIR IN FLUID LINE THE SAME

This application is a continuation of application Ser. No. 08/564,548 filed on Nov. 29, 1995, now abandoned.

FIELD OF THE INVENTION

The present invention relates generally to detection of air bubbles in fluid flow lines, and, more particularly, to an optical detector which discriminates between air and saline solution in a section of flexible tubing, on the basis of the different indices of refraction of air and saline solution.

BACKGROUND

In dispensing fluids for medical purposes, for example, in infusing saline solution intravenously into a patient's vein, it is important to assure a flow of fluid which is not interrupted by an air bubble. Such a bubble, in a tubing line between the fluid bottle and the intravenous needle, may not only interfere with the intended continuous administration of fluid, but may be dangerous to the patient if the bubble travels into the bloodstream, where it could cause an embolism. In medical analysis instrumentation, it is also important to detect bubbles.

It is known from U.S. Pat. No. 4,366,384, JENSEN, to direct a beam of light through a fluid-carrying transparent tube, and to discriminate between fluid and air by measuring the intensity of light leaving the tube. However, if the fluid used is clear, it is difficult to obtain an unambiguous reading by this method.

It is known from U.S. Pat. No. 4,859,864, SMITH, to reflect a light beam off an interior surface of a transparent tube, in such a way that no light is detected when fluid is in the tube, but light is detected when an air bubble is in the tube.

It is known from U.S. Pat. No. 4,884,065, CROUSE et al., to clamp a cylindrical tubing segment 12A or 12B into a V-shaped recess 24 and to discriminate (cf. FIG. 6) between fluid and water, based on the exit angle of a light beam from the tubing. However, in this design, any "distortion" of the tubing shape due to clamping is incidental (cf. col. 8, line 4).

PASCAL/HEMOCARE S. A. French unexamined application 2 660 755 A1 discloses an optical detector in which, in the absence of liquid (FIG. 3), light is scattered in different directions 18 and fails to reach a detector 4, while in the presence of liquid (FIG. 4), light follows a trajectory 15 which reaches detector 4.

PLATT et al. published PCT application WO 86-04409 (31 Jul. 1986) discloses an optical detector in which a tube 12 is placed on a platform or cradle 16, in such a way that a light beam reaches a sensor 12 when the tube contains air, but is refracted or scattered away from the sensor 12 when the tube contains fluid. However, no shaping of the tubing occurs in this device.

SUMMARY OF THE INVENTION

The present inventors have discovered that ambiguity, in readings from an optical bubble detector used with tubing, can be reduced by shaping the tubing into the shape of a prism, so that when different contents of the tubing have differing indices of refraction, there is a clear difference in the exit angle of the light beam leaving the tube. A triangular prism shape is preferred.

Accordingly, the present invention features an optics block formed with a V-shaped recess, and a clamp block. The optics block and clamp block cooperatively press or "sandwich" the flexible tubing into the V-shaped recess and deform it into a triangular prismatic cross-section. A generally U-shaped optical interrupter element, containing a photoemitter and a photosensor, fits into the optics block in such a manner that a light beam is directed radially into the triangular tubing section. The clamp block "windows" the transmitted and received light from the optical interrupter, to allow only a thin channel of light to be transmitted; this minimizes optical noise during measurement.

When saline is located in the tubing, the light follows a fairly straight path through the optics block and tubing. However, when air is in the tubing, the light is refracted away from the photosensor, resulting in lower intensity readings. By measuring the amount of light received at the photosensor, it can be determined whether air, or saline, is in the tubing. The measurement values which correspond respectively to air and to saline can be determined by one of ordinary skill in the art without undue experimentation.

BRIEF FIGURE DESCRIPTION

FIGS. 13–16 are, respectively, side, end, top and bottom views of the photoemitter/photosensor module;

DETAILED DESCRIPTION

Figure 1:
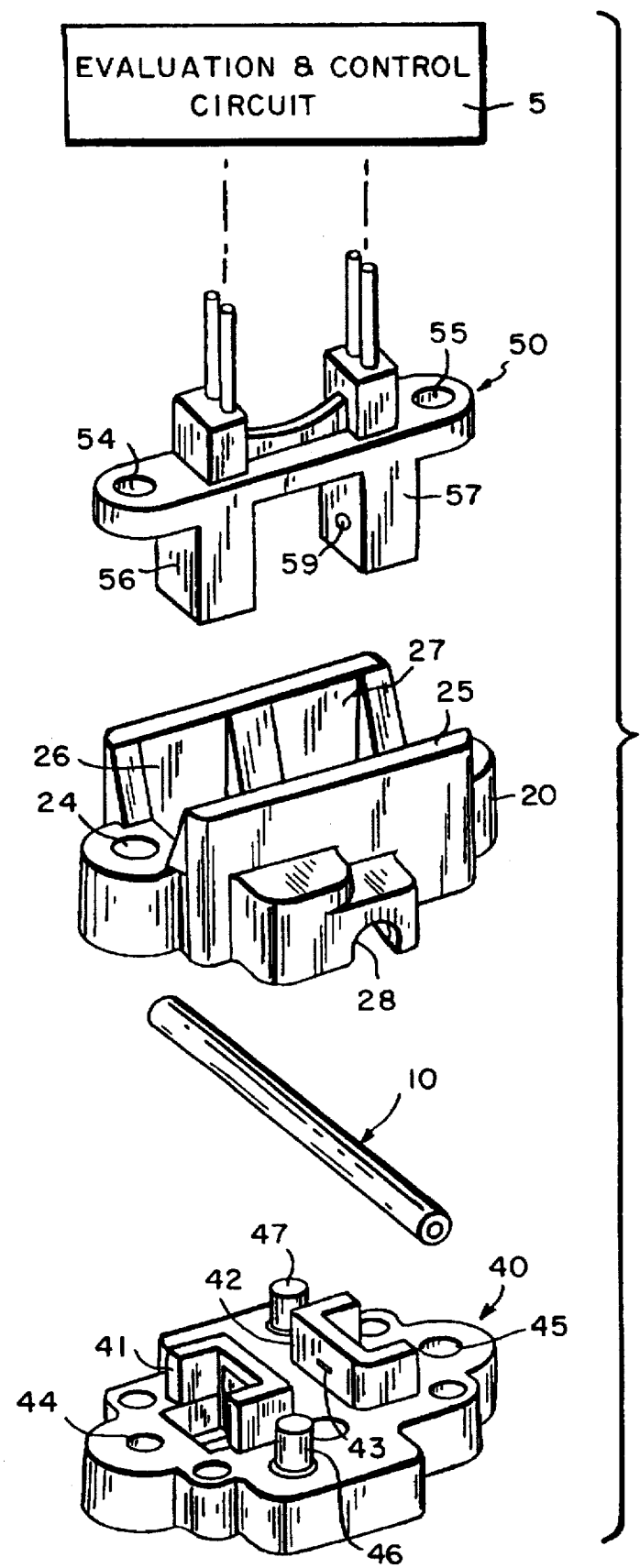
FIG. 1 is an exploded perspective View of the 4 principal mechanical modules of the bubble detector of the present invention, with the electrical leads shown broken away.

FIG. 1 illustrates schematically a segment of flexible tubing 10 which is placed in a channel defined by the upper surface of a clamp block or support block 40, which has a pair of C-shaped vertical projections 41 and 42, whose long faces form the sides of the channel. There is a small window 43, through each of these long faces, for passage of a beam of light. An optics block or shaping mold 20, formed with a recess 28, is pressed down over tubing 10 to deform the tubing into the desired cross-sectional shape. Tubing 10 is suitably made of Fluorinated Ethylene Propylene (FEP) Copolymer, 90 durometer, or polyurethane, with an inner diameter of 0.063 inch (0.160 cm), a wall thickness of 0.014 inch (0.0356 cm), plus or minus 10%, and an outer diameter of about 0.091 inch (0.23114 cm).

However, if one were willing to sacrifice compatibility with standard tubing sets, one could practice the present invention with a permanently-formed transparent tube of the desired cross-sectional shape. Shaping an originally cylindrical section of flexible tubing into a triangular cross-section is more advantageous than introducing another element with a triangular cross-section because introducing another element in the middle of a length of cylindrical tubing will inevitably create an irregular surface at the "splice" or other transition point. Such an irregular surface tends to trap bubbles, leading to false sensor readings or an increase in the number of bubbles, which the invention is designed to detect and counteract.

A photoemitter/photosensor module 50 then slides into the assembled optics and clamp blocks until the photoemitter and photosensor are aligned with windows 43 to define a beam passage. The left and right edges of elements 20, 40, and 50 are formed with respective left vertical holes 24, 44, 54 and respective right vertical holes 25, 45, 55 to permit insertion of fasteners to secure them together. Module 50 is preferably formed with a left downward projection 56 containing the photoemitter 58 and a right downward projection 57 containing the photosensor 59. These projections 56, 57 fit into correspondingly-shaped wells 26, 27 in optics block 20, in order to further facilitate alignment. Further, clamp block 40 has two upwardly projecting pins 46, 47 which fit into mating recesses in the underside of optics block 20. Element 20 preferably comprises polysulphone plastic, while element 40 preferably comprise polycarbonate plastic. Element 50 can be any standard plastic with a compatible coefficient of thermal expansion (CTE). This facilitates injection-molding.

Figure 2:
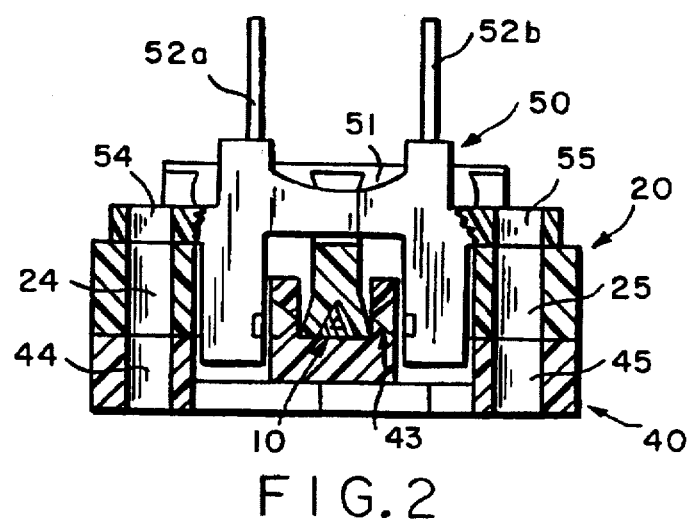
FIG. 2 is a cross-sectional view of components of FIG. 1 after assembling them together.

FIG. 2 is a cross-sectional view of the above-described modules in the assembled state. Tubing 10 is pressed into a cross-sectional shape which is generally an equilateral triangle. Projections 56, 57 of module 50 rest inside wells of blocks 20 and 40, with the photoemitter and photosensor aligned with windows 43 of clamp block 40. A bridge portion 51 of module 50 connects the two projections 56, 57, and respective pairs of photoemitter electrodes 52a and photodetector electrodes 52b project out the top of module 50, for connection to an evaluation circuit 5, shown schematically in FIG. 1. The evaluation circuit could employ, for example, a MOTOROLA microcontroller model 68HC16Z1CFC16 having a 10-bit input to an Analog/Digital Converter (ADC) forming a part thereof. Having the light intensity measurements in digital form facilitates calibration and further processing.

Figure 3:
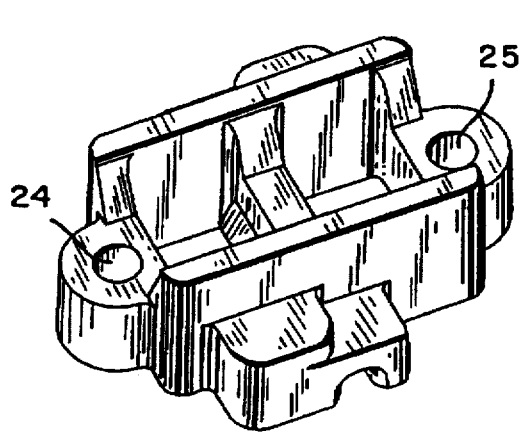
FIGS. 3 and 4 are, respectively, top and bottom perspective views of the optics block shown in FIG. 1.

FIG. 3 is a top perspective view of optics block 20, again showing left and right vertical holes 24, 25.

Figure 4:
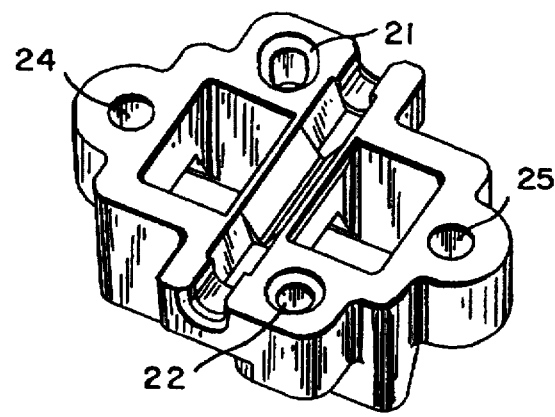

FIG. 4 is a bottom perspective view of optics block 20, showing recess 21 which receives pin 46 of clamp block 40 and recess 22 which receives pin 47 of clamp block 40.

Figure 5:
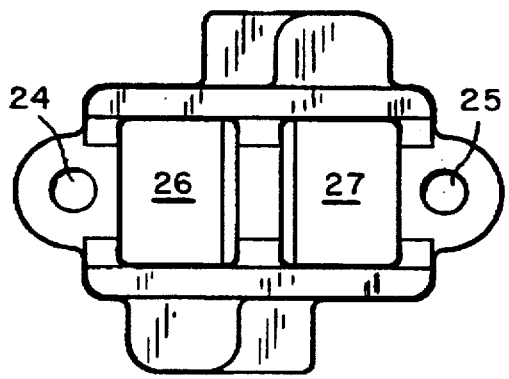
FIGS. 5 and 6 are, respectively, top and side views thereof.

FIG. 5 is a top plan view of optics block 20, showing the generally rectangular shape of wells 26, 27.

Figure 6:
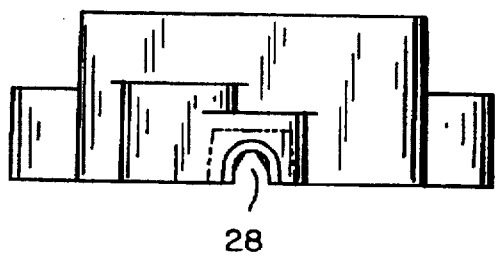

FIG. 6 is a side view of optics block 20, showing that recess 28 is generally semi-cylindrical at each end, but becomes V-shaped along a central longitudinal portion thereof.

Figure 7:
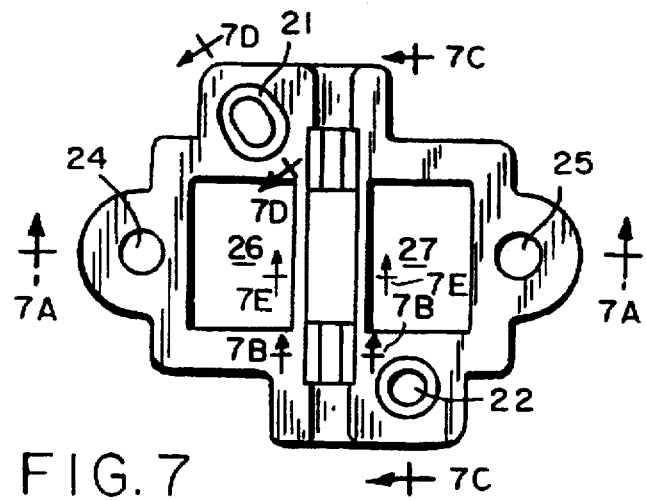
FIG. 7 is a bottom view thereof.

FIG. 7 is a bottom view of optics block 20, showing the section lines for subsequent cross-sections.

Figure 7A:
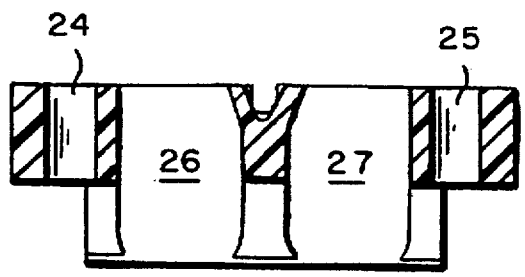
FIGS. 7A–7E are sections taken along the section lines indicated in FIG. 7.

FIG. 7A is a cross-section along line 7A—7A of FIG. 7, showing the V-shaped groove in recess 28.

Figure 7B:
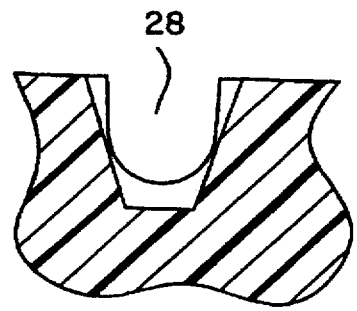

FIG. 7B is a cross-section along line 7B—7B of FIG. 7, showing the semi-cylindrical portion of recess 28.

Figure 7C:
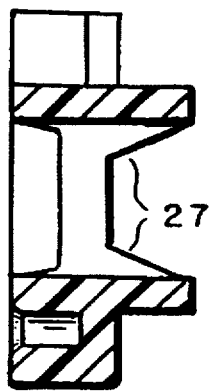

FIG. 7C is a section along line 7C—7C of FIG. 7, showing the tapered sidewalls of well 27.

Figure 7D:
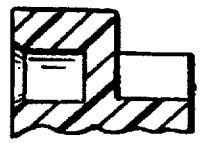

FIG. 7D is a cross-section along line 7D—7D of FIG. 7, showing the shape of recess 21.

Figure 7E:
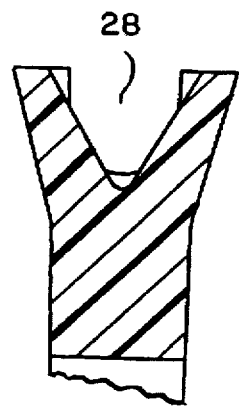

FIG. 7E is an enlarged cross-section of the V-shaped groove, showing that it preferably has a Y-shaped element 7 which defines a 60 degree angle within the fork of the Y. Element 7 fits snugly within the rest of optics block 20.

Figure 9:
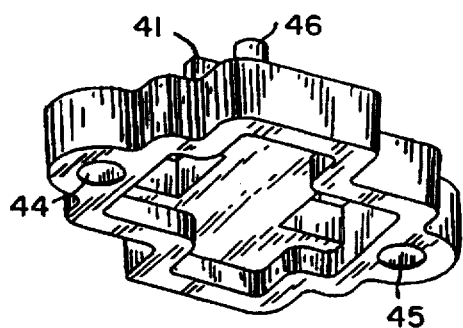
FIGS. 8 and 9 are, respectively, top and bottom perspective views of the clamp block shown in FIG. 1.
Figure 8:
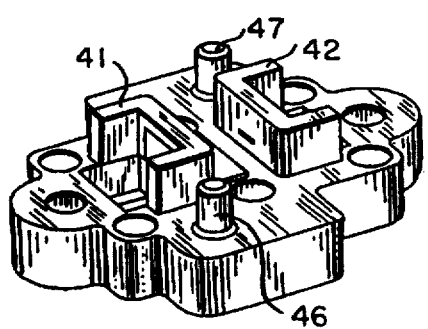
Figure 10:
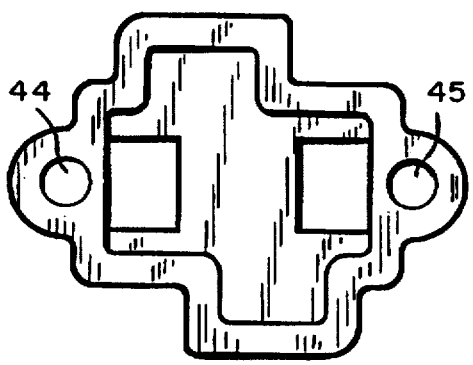
FIGS. 10 and 11 are, respectively, bottom and side views thereof.
Figure 11:
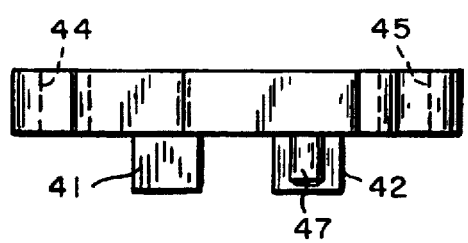

FIG. 8 is a top perspective view of clamp block 40, and FIG. 9 is a bottom perspective view thereof. FIG. 10 is a bottom plan view thereof. FIG. 11 is an inverted side view thereof.

Figure 12:
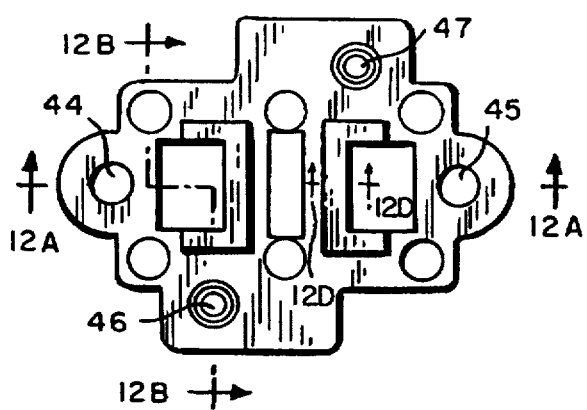
FIG. 12 is a top view thereof.

FIG. 12 is a top plan view, showing section lines used in the subsequent figures.

Figure 12A:
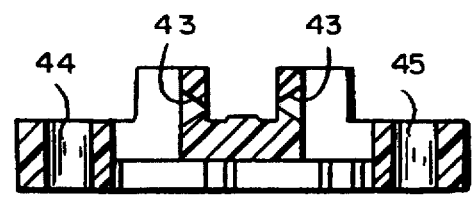
FIGS. 12A, 12B, and 12D are sections taken along the section lines indicated in FIG. 12.
Figure 12B:
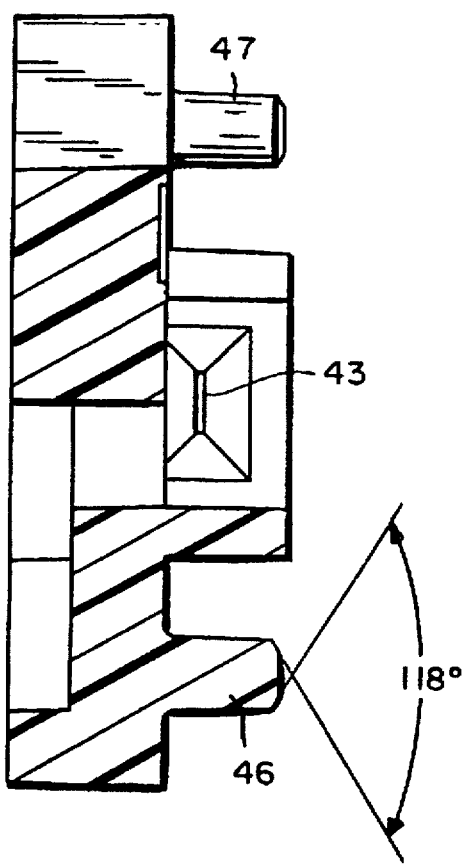
Figure 12C:
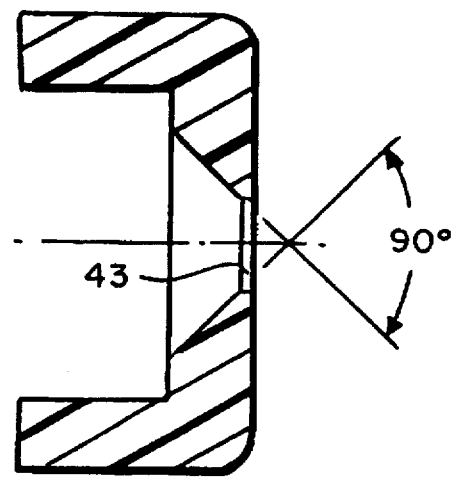
FIG. 12C is a section taken along the the section line indicated in FIG. 12E.

FIG. 12A is a sectional view along line 12A—12A of FIG. 12, showing the flared cross-sections of windows 43 in projections 41, 42. FIG. 12B is a section along staggered line 12B—12B of FIG. 12, showing the height of projection 41. FIG. 12C is a section of FIG. 12E, showing that window 43 preferably has a 90 degree flare in the horizontal dimension.

Figure 12D:
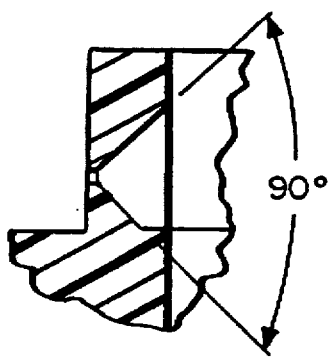

FIG. 12D is an enlargement of a detail of FIG. 12A, showing that window 43 preferably has a 90 degree vertical flare, also. Preferred dimensions of window 43 are 0.010" (0.0254 cm) ±0.001" (0.00254 cm)×0.08" (0.2032 cm) ±0.005" (0.0127 cm).

Figure 12E:
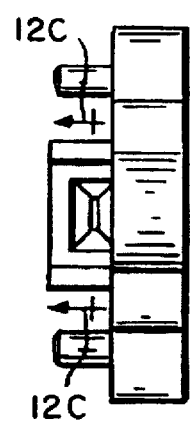
FIG. 12E is an end view thereof.

FIG. 12E is a side view of projection 41 or 42, which are essentially mirror images of each other.

FIG. 13 is an enlarged, inverted side view of the photo module 50. FIG. 14 is an end view thereof. FIG. 15 is a top view showing the electrodes protruding from photoemitter and photosensor. Elements 50, 51, 52A+B, and 54–59 are all purchased as a unit from OPTEK Technology, Inc. under their Part No. OPB9940. The photoemitter 58 is preferably a light-emitting diode having a maximum power dissipation of 100 milliwatts and a forward DC current of 50 milliamps. The photosensor 59 is preferably a phototransistor having a collector-emitter voltage of 30 volts max and an emitter-collector voltage of 5 volts max. Its power dissipation is also about 100 milliwatts. Preferably, when photoemitter 58 has an input current of about 25 milliamps, photodetector 59 has an output current in the range 3–9 milliamps. The wavelength of light used is preferably about 940 nanometers in the infra-red range, although other wavelengths are also suitable. Wavelengths outside the visible range (400–700 nanometers) are preferred.

Figure 17:
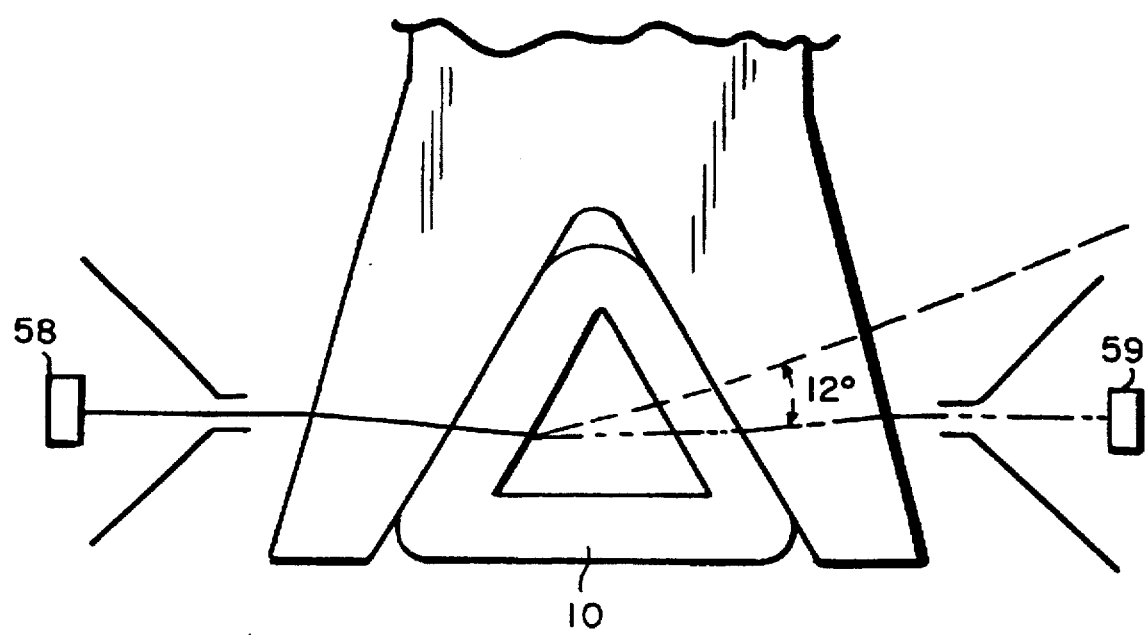
FIG. 17 is a ray diagram, illustrating schematically how the exit angle of the light beam differs as a function of refractive index of the medium through which the beam passes inside the tube.

FIG. 17 is a ray diagram, showing that, when saline is in the tubing, the exit angle of the ray or beam is substantially the same as the entry angle, while when air is in the tubing, the exit angle is about 12 degrees higher than with saline, so that the beam will miss the photosensor 59 when air is present. In an alternate embodiment (not shown), one could align the detector to receive the light beam when air is present, and not to receive the light beam when saline is present. CALIBRATION OF SENSOR, AND EVALUATION OF SENSOR OUTPUT SIGNALS In order to determine which sensor output levels indicate air in the tubing and which levels indicate saline in the tubing, it is necessary to first assemble the optics block, tubing, and clamp block together, then calibrate the sensor. This calibration compensates for manufacturing variations in the tubing inner diameter (I.D.), tubing outer diameter (O.D.), and possible distance between the centers of the outer surface of the tubing and the inner surface of the tubing. If the outer surface and the inner surface do not define perfectly concentric circles, these centers will not coincide with each other.

Figure 18:
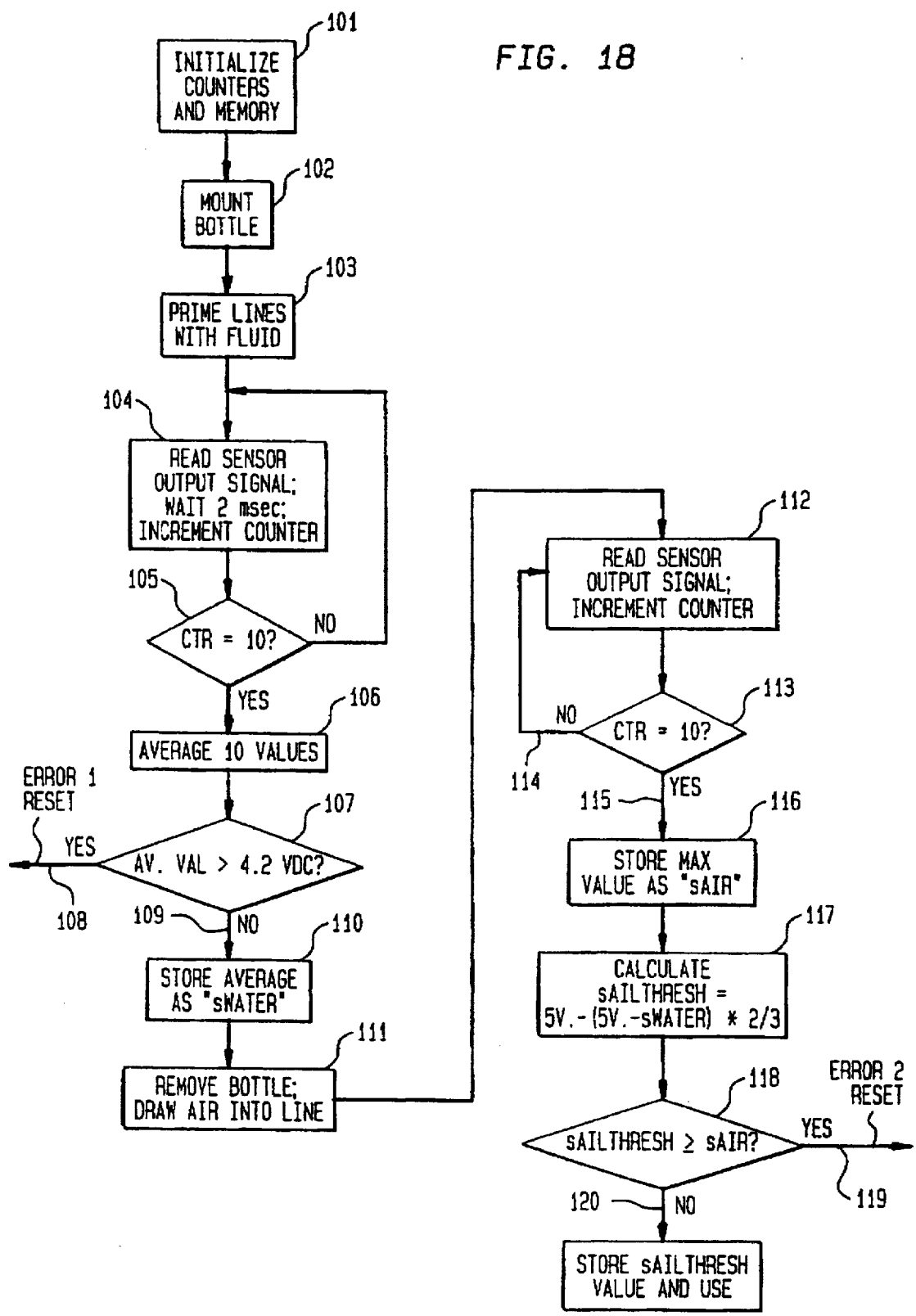
FIG. 18 is a flowchart of the sensor calibration process.

FIG. 18 illustrates the steps in the calibration process. This process is preferably carried out using a routine written in the computer language C, running in the MOTOROLA microcontroller model 68HC16Z1CFC16 mentioned above. In a step 101, counters and memory are initialized. Then, in step 102, the fluid bottle is mounted by the user, in response to a prompt on a display screen. The tubing lines are primed (filled) with fluid from the bottle in step 103. In step 104, the electrical output signal of the photosensor is then read (sampled), and, after a delay of 2 milliseconds, a counter is incremented. At step 105, a test is performed to see if the contents of the counter has reached the value 10. If not, another reading is taken by repeating step 104. If the value 10 has been reached, the ten sensor output values are averaged in a step 106. At step 107, this average value is tested to determine if it exceeds 4.2 volts DC. If yes, this is considered an "ERROR 1" condition, and operator intervention is required. If not, a decision branch 109 leads to step 110, which stores the average value as "sWater." Then, in step 111, the bottle is removed by the user, and sufficient air is drawn into the tubing line to assure that there is air in the light path of the sensor. In a step 112, analogous to step 104, the sensor output signal is read and a counter is incremented. A test 113, analogous to step 105, is performed to check whether 10 readings have been taken yet. If not, a decision branch 114 leads back to step 112. If yes, a decision branch 115 leads to a step 116, in which the largest of the ten readings is stored as "sAir." Thereafter, a threshold value sAilthresh is calculated in step 117 by evaluating the equation $5 V-(5 V -sWater)* \frac{2}{3}$, where V means volts. A final test 118 checks whether sAilthresh is greater than or equal to sAir. If yes, an "Error 2" condition is considered to exist, and operator intervention is required. If not, the process follows decision branch line 120, sAilthresh is considered correct, and this value is stored as the calibrated threshold value of the sensor, for discriminating between the fluid-in-line condition and the air-in-line condition. That is, when the sensor output signal is below sAilthresh, an "air-in-line" indication is generated, while when the signal is above sAilthresh, a "fluid-in-line" state is considered to exist.

After the sensor is assembled and calibrated, there is little variation, due to tubing geometry, in the signal output level representing air and the sensor output level representing saline.

Variation of the size of the aperture 43 in the clamp block affects how much light is transmitted into the tubing. Variations in the slot width result in a scaling of both the air signal level and the saline signal level. Larger slot widths result in larger received currents (which results in a lower voltage). This scaling factor is accounted for by the calibration process.

Various changes and modifications are possible within the scope of the inventive concept. Therefore, the invention is not limited to the specific embodiment shown and described, but rather is defined by the following claims.

What is claimed is:

1. An optical detector for air in a normally fluid-filled transparent flexible tubing line (10), comprising
   a photoemitter (58) adapted to emit a light beam;
   a photosensor (59) aligned to receive said light beam;
   a support block (40) which positions said transparent tubing line to intersect said light beam; and
   a shaping mold (20) which presses said tubing line (10) into a predetermined cross-sectional shape, in order to maximize a difference in exit angle Of said light beam, from said tubing line, depending upon whether said beam passes through fluid, having a first index of refraction, or through air, having a second, differing, index of refraction.

2. An optical detector as recited in claim 1, wherein said predetermined cross-sectional shape is a triangle.

3. An optical detector as recited in claim 1, further comprising a photo module (50) having two projecting portions (56, 57) within which said photoemitter (58) and photodetector (59) are respectively supported; and
   said shaping mold (20) is formed with respective wells (26,27) into which said projecting portions (56,57) are received.

4. An optical detector as recited in claim 1, wherein said support block (40) is formed with
   a first window (43), through which a light beam from said photoemitter (58) passes before entering said tubing (10) and
   a second window (43), through which a light beam leaving said tubing (10) must pass, in order to reach said photosensor (59).

5. An optical detector as recited in claim 1, further comprising an evaluation and control circuit (5) having output terminals connected to electrodes of said photoemitter (58) and input terminals connected to electrodes of said photosensor (59).

* * * * *

UNITED STATES PATENT AND TRADEMARK OFFICE
CERTIFICATE OF CORRECTION

PATENT NO. : 5,672,887
DATED : September 30, 1997
INVENTOR(S) : Benjamin G. Shaw, et. al.

It is certified that error appears in the above-identified patent and that said Letters Patent is hereby corrected as shown below:

Column 1, Line 34: Delete "when-fluid" and insert --when fluid--.

Column 6, Line 18: Delete "Of" and insert --of--.

Signed and Sealed this

Tenth Day of November 1998

Attest:

BRUCE LEHMAN

Attesting Officer    *Commissioner of Patents and Trademarks*